United States Patent [19]

Smith et al.

[11] Patent Number: 4,823,788
[45] Date of Patent: Apr. 25, 1989

[54] DEMAND OXYGEN CONTROLLER AND RESPIRATORY MONITOR

[76] Inventors: Richard F. M. Smith, 1571 Mulberry Ave., Upland, Calif. 91786; Robert G. Irvine, 1393 Carthage Ct., Claremont, Calif. 91711

[21] Appl. No.: 182,456

[22] Filed: Apr. 18, 1988

[51] Int. Cl.$^4$ .............................................. A62B 9/02
[52] U.S. Cl. ........................... 128/205.24; 128/204.18; 128/204.21; 128/205.11
[58] Field of Search ........... 128/716, 719, 724, 204.18, 128/204.21, 204.22, 205.11, 204.26, 205.24; 73/24

[56] References Cited

U.S. PATENT DOCUMENTS

| | | | |
|---|---|---|---|
| 4,019,382 | 4/1977 | El-Gammel | 128/724 |
| 4,506,666 | 3/1985 | Durkan | 128/204.23 |
| 4,570,631 | 2/1986 | Durkan | 128/204.23 |
| 4,596,133 | 6/1986 | Smalling et al. | 73/24 |

Primary Examiner—Edgar S. Burr
Assistant Examiner—Aaron J. Lewis
Attorney, Agent, or Firm—Walter F. Wessendorf, Jr.

[57] ABSTRACT

An improved method and apparatus for controlling the flow of any breathing gas such as oxygen through a cannula or "mask" to a person (patient, aviator, baby, miner, or diver) can be limited to the portion of the breathing cycle when the person breathes inward. This has the effect of reducing the consumption of breathing gas to at least half and possibly less. The result of this reduction of consumption is an extended life of the gas supply and a reduction of the cost per unit time. A bidirectional dynamic mass flow sensor senses the rate of flow of a gas through it and yields an output voltage proportional to mass flow and direction of gas movement. The measured dynamic flow signal is applied to a system controller which operates a flow controller. The system controller provides for indications of operation such as system failure and apnea, rate of flow, duration of flow, and total consumption; in addition, controls are provided to set the duration of gas flow in each breathing cycle.

16 Claims, 1 Drawing Sheet

DEMAND OXYGEN CONTROLLER AND RESPIRATORY MONITOR

BACKGROUND OF THE INVENTION

1. Technical Field

This invention relates to a method and apparatus of a demand oxygen controller and respiratory monitor for measuring and monitoring gaseous fluid flow and particularly gas flow from persons (patients, aviators, babies, miners, or divers).

2. Background

In the prior art, the practice is to use a fluidic sensor which only monitors breathing direction; or the method therefor has been adapted for demand oxygen control only but has not been adapted to mass flow or apnea detection.

3. This Invention

In this invention of the demand oxygen controller and respiratory monitor for mass flow measurement, the actual mass and direction of the gas, compensated for density and temperature, passing a certain point is measured. In flow measurement that does not compensate for density and temperature, the mass of the gas is unknown. In a mass flow measurement, the amount of gas molecules being either inspired or expired is known accurately because of the automatic compensation for density and temperature by the mass flow sensor. Thus, if a patient's expired breath is a different temperature than the inspired gas being fed to the patient, the mass flow, both ways, is accurately measured by the mass flow sensor and indicated by a particular output voltage in each respective direction. The patient is dependent upon the number of molecules of gas being supplied and this is dependent upon the barometric pressure and temperature surrounding the patient. Since the mass flow sensor is capable of accurately measuring mass flow regardless of the gas temperature, the oxygen demand controller can accurately control the mass of oxygen suppled to a patient regardless of whether the gas is supplied from an oxygen supply tank at room temperature or from a heated oxygen supply. For example, a pilot at a high altitude requires a higher flow rate of oxygen for the same mass per unit time than a deep sea diver inhaling oxygen at the higher barometric pressure. This is because there are more molecules of gas passing through the mass flow sensor at the higher barometric pressure. Thus, the arterial oxygen tension ($P_aO_2$) present in the blood stream is dependent upon the mass, not the volume, of oxygen inhaled at a specific barometric pressure. As a result, the percentage of oxygen present at a particular volume of gas must change in accordance with the barometric pressure. For example, a pilot must have a higher percentage of oxygen per breath than a deep sea diver in order a maintain a given arterial oxygen tension in the blood stream.

This apparatus is considerably smaller and less complex than previous devices. It has additional features such as mass flow rate, respiratory rate, and cessation of breathing.

*U.S. Pat. No. 4,570,631 attempts to detect apneic events through the use of a fludic means. This device is physically large and cumbersome. Its main purpose is to supply a high pressure pulse of gas or an electric shock to the patient to dislodge an obstruction or otherwise open the upper airway passage. It does not measure mass flow nor control the flow of breathing oxygen to a patient.

SUMMARY OF THE INVENTION

Accordingly, the objects of the invention are to contribute to the solution of the discussed problems of the prior-art by providing mass flow, increased sensitivity, miniaturization and apnea detection. These additional features permit application of this apparatus to persons having a near zero breath (very small mass flow) such as babies and persons near death to an extremely strong breath in healthy persons. This apparatus can be used to control the mass flow of oxygen to persons such as patients, miners, divers, and aircraft personnel. It will also monitor a person's breathing rate, mass flow rate, and cessation of breathing. Some of the important features of the controller are its ability to reduce the consumption of oxygen without significantly reducing the arterial oxygen tension ($PaO_2$) of a patient, and its ability to initiate an apnea alarm in case of a patient's respiratory distress. It's low cost will make it affordable to all anesthesiology departments especially those that must monitor the respiratory functions of a patient who has been administered any of the drugs in the Morphine family which cause respiratory depression to the point of apnea. The cost of supplemental oxygen and other breathing gasses remains substantial. With prior-art continuous flow systems, a substantial portion of the oxygen is wasted. The controller of this invention will substantially reduce such waste of oxygen and thereby increase the efficiency of supplemental oxygen systems. Versions of the controller can be used with room air to monitor breathing of babies and adults that might be subject to an apnea syndrome, providing an alarm in case of apnea.

The method and the apparatus according to the invention are in particular applicable to hospital patients, ambulatory patients, babies, divers, miners, and aviators who receive supplemental oxygen through a cannula, tracia tube, or "mask."

BRIEF DESCRIPTION OF THE DRAWINGS

The invention may be more fully understood by reading the following description in conjunction with the appended drawing.

DETAILED DESCRIPTION OF THE PREFERRED EMBODIMENT

Figure 1:
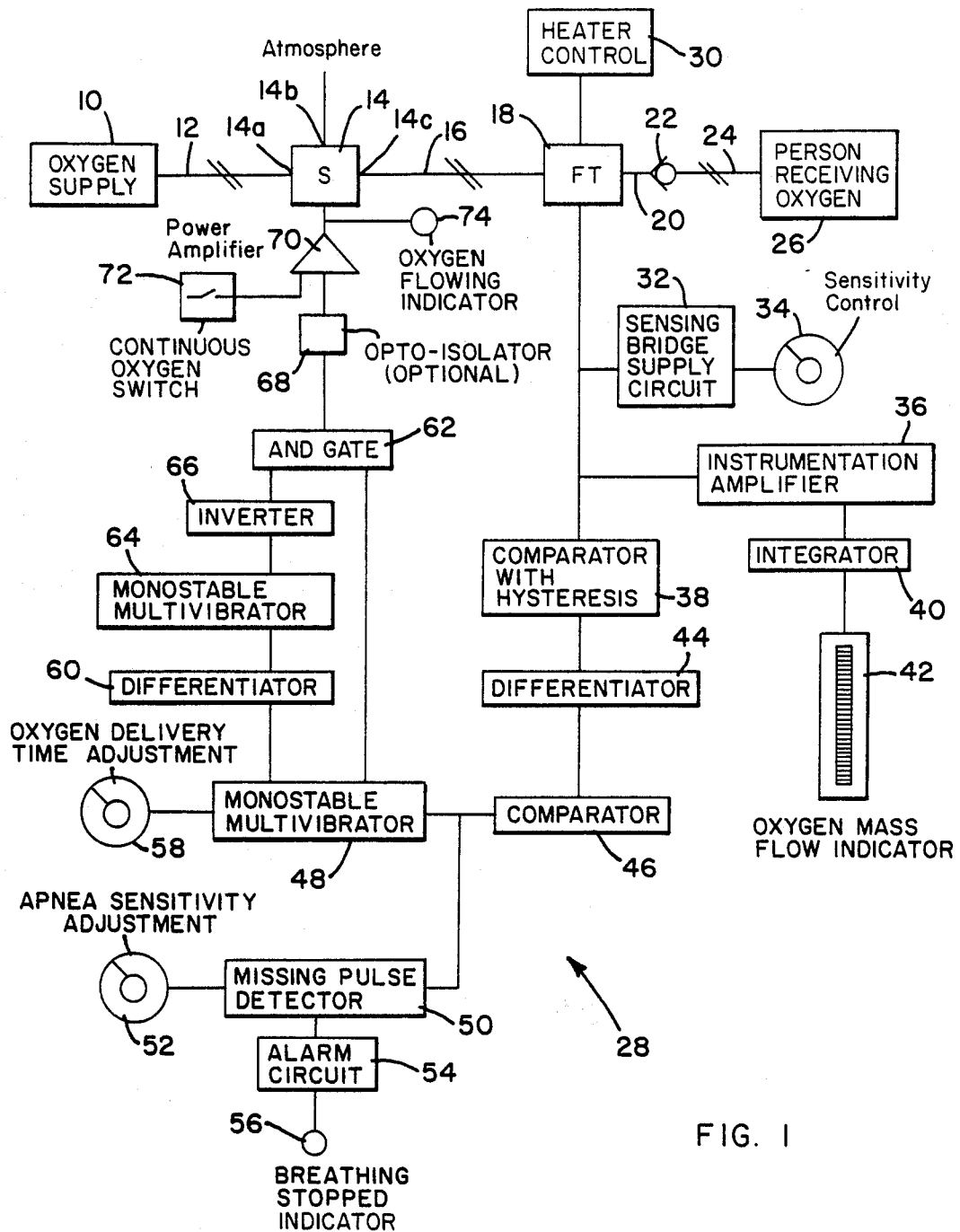
FIG. 1 is a block diagram showing an example of how the present invention is to be used.

The system of the embodiment shown in FIG. 1 comprises a source of gas 10 connected, for communicative relationship, via line 12 to port 14a of a valve means 14 that is a three-way, two-position, solenoid-actuated spool valve having additional ports 14b and 14c. Valve port 14c communicates via line 16 with a mass flow sensor 18 of the type manufactured by Micro Switch, a Division of Honeywell, per its August 1987 publication specification PK 8854 0 for its AWM2000 Series. Line 20 communicates with such mass flow sensor 18 and is connected to an in-line check valve or bacterial filter 22 which, in turn, is connected via line 24 to a person 26 receiving gas 10. Bacterial filter 22 operates like a check valve in the sense that, upon the flow of expiration gasses from such person 26 to the mass flow sensor 18, bacteria contained in such person's expired gasses will not contaminate the mass flow sensor 18. The inspired and expired gasses from person 26 use common lines 16, 20 and 24. Therefore, check valve 22, upon being replaced by a bacterial filter, prevents contamination of the mass flow sensor 18 by bacteria contained in such person's expired gasses. Port 14b of valve means 14 vents line 16 through port 14c of valve means 14 to atmosphere so that the inspiration gasses of such person 26 pass through ports 14b and 14c of valve means 14, line 16, mass flow sensor 18, line 20, bacterial filter 22, line 24 to such person 26. Port 14b of valve means 14 vents line 16 through port 14c of valve means 14 to atmosphere so that the expiration gasses of such person 26 pass through bacterial filter 22, line 20, mass flow sensor, line 16, ports 14c and 14b of valve means 14 to atmosphere. The mass flow of gasses thrugh the mass flow sensor 18 results in an electrical output voltage proportional to the magnitude and direction of such mass flow. Such electrical output voltage through electronic circuitry, generally referred to by reference numeral 28, controls the solenoid valve 14. heater control 30 is required for the proper operation of the mass flow sensor 18 per the cited Micro Switch specification. Such heater control 30 is uniquely adapted to the mass flow sensor 18 to provide an output to minimize errors due to ambient temperature changes. Heater control 30 is designed to keep the mass flow sensor 18 heater temperature for the dual sensing resistors, located inside the mass flow sensor 18, at a constant differential above ambient air temperature under varying temperature and air flow. The circuitry for the heater control 30 is shown in the cited Micro Switch specification. Ambient temperature is sensed by a similar heatsunk resistor located inside the mass flow sensor 18. A sensing bridge supply circuit 32 is required per the cited Micro Switch specification for the proper operation of the mass flow sensor 18. The sensing bridge supply circuit 32 is two of the arms of a Wheatstone bridge. The other two arms are dual sensing resistors, located inside the mass flow sensor 18, which are the two active arms of the Wheatstone bridge. The sensing bridge supply circuit is likewise shown in the cited Micro Switch specification. The differential voltage output from the sensing bridge supply circuit 32 is also the differential voltage across the two active arms of the Wheatstone bridge circuit. Sensitivity control 34 allows a human operator to control the sensitivity of the sensing bridge supply circuit 32. As the direction of air flow through the mass flow sensor 18 is reversed, the polarity of the differential output voltage from such mass flow sensor 18 also reverses. Such differential output voltage is applied to the instrumentation amplifier 36 and the comparator with hysteresis 38. Instrumentation amplifier 36 conditions and outputs a signal proportional to mass flow to integrator 40. The output signal from integrator 40 is applied to the oxygen mass flow indicator 42 which may be analog, digital, or graphical. Comparator with hysteresis 38 operates on the differential output voltage which is a slowly varying voltage proportional to the direction and flow of such person's breath. Comparator with hysteresis 38 speeds up such slowly varying voltage to one of two instantaneous voltage levels. A differentiator 44 and a comparator 46 condition the negative going level from the comparator with hysteresis 38 into a negative pulse. Such negative pulse in turn triggers a monostable vibrator 48 and a missing pulse detector 50. An apnea sensitivity adjustment 52 allows such human operator to adjust the time interval that a person does not breathe before the missing pulse detector 50 senses apnea. When the missing pulse detector 50 senses apnea, it outputs a signal to an alarm circuit 54 which turns on a breathing stopped indicator 56. The breathing stopped indicator 56 may be either an audible alarm or a visual indicator, such as an LED or an incandescent lamp. An oxygen delivery time adjustment 58 permits such human operator to adjust the time interval of the monostable multivibrator 48 which, in turn, supplies a wide, timed positive voltage pulse to a differentiator 60 and an AND gate 62. The width of such timed voltage pulse from the monostable multivibrator 48 is equal to the time that oxygen from the oxygen supply 10 is delivered to such person 26. The differentiator 60 applies a negative pulse at the end of such positive time interval to a monostable multivibrator 64. The monostable multivibrator 64 provides a time delay necessary for pneumatic oscillations in line 16 to decay and during which time oxygen is prevented from being supplied to such person 26. The output voltage pulse from the monostable multivibrator 64 is inverted by an inverter 66 and then applied to the AND gate 62. The output signal from the inverter 66 and the monostable multivibrator 48 are combined by the AND gate 62 to provide an output signal dependent only upon such person's breathing and not upon the pneumatic oscillations in line 16. The AND gate 62 provides an output signal to an opto-isolator 68 which in turn drives the input of a power amplifier 70. A continuous oxygen switch 72 permits the human operator to override the signal from the opto-isolator 68 thus supplying continuous oxygen to such person 26. Output from the power amplifier 70 controls valve 14 and an oxygen flowing indicator 74. Thus it can be understood that the controller provides a timed negative output signal to de-energize the solenoid of valve means 14 to dispose the spool of valve means 14 in its open position, with port 14b of valve means 14 remaining closed, to establish downstream communication from the source 10 of breathing gas, such as oxygen, through line 12, communicating ports 14a and 14c of valve means 14, line 16, mass flow sensor 18, line 20, bacterial filter 22, line 24 to such person 26 receiving oxygen. Such timed negative output signal from the controller equals the time that oxygen is being supplied to such person 26 during each of the very initial stages of such person's inspiration cycles. Thus, the loss of power to the solenoid results in continuous oxygen from source 10 being supplied to such person 26 in the manner described above and commonly referred to as a fail-safe mode. And that, at the end of each timed negative output signal during the very initial stages of such person's inspiration cycles, the controller provides a positive output signal which energizes the solenoid of valve means 14 to dispose the spool of valve means 14 in its closed position to close port 14a and open port 14b of valve means 14 to establish upstream communication from such person 26 who had been supplied breathing gas, such as oxygen, and through line 24, bacterial filter 22, line 20, mass flow sensor 18, line 16, communicating ports 14c and 14b of valve means 14 to vent to atmosphere from port 14b of valve means 14 such person's remaining inspired gasses and, provided the check valve 22 was replaced by the bacterial filter, to also vent to atmosphere such person's expired gasses. While the invention has been particularly shown and described with reference to the preferred embodiment therefor, those skilled in the art will understand that various alterations in form and detail may be made therein without departing from the scope of the invention. For example, the functional circuitry can be implemented using a microprocessor, state machine, EPROM, or PAL. Moreover, while the invention has been particularly shown and described with reference to a cannula adapted for clinical use, it should be understood that the invention can be used in other fields, such as gas supply or apnea detection for persons in neonatal, aeronautical, subterranean or underwater environments.

OPERATIONAL DESCRIPTION

A person 26 using this invention would place a cannula in such person's nostrils. A technical person would adjust the sensitivity control 34 based upon the intensity of the inspired breath of the person using the invention. For example, sensitivity would vary depending upon whether the person using the invention is a neonatal infant or healthy adult. This is a screwdrive adjustment normally only made once by a technical person rather than the person using this invention. Apnea sensitivity adjustment 52 is set such that a normal breathing pattern for the person does not produce an alarm by an alarm circuit 54. Since the breathing rate and intensity of inspiration depends upon the person using this invention, the apnea sensitivity adjustment 52 is normally set to indicate the loss of two to four successive breaths based upon the person's breathing rate. The oxygen delivery time adjustment 58 is set to control the amount of time during the very initial stage of each inspiration cycle that oxygen is delivered to the person brething. This delivery time adjustment 58 should be set so that proper arterial tension ($PaO_2$) of the person is maintained in accordance with the attending physician's orders. If breathing ceases, breathing stopped indicator 56 would signify the presence of apnea. This invention would also allow a person using a portable oxygen tank to use the oxygen supply 10 for a longer period of time because oxygen flows only during a portion of inspiration cycle; oxygen is not wasted during the balance of the inspiration cycle nor during any of the expiration cycle. In another application, a cannula is inserted in the nostrils of a neonatal baby, young infant, or other person 26 susceptible to apnea; oxygen need not be supplied in this application. A simplified version not employing the solenoid valve 14 and associated driving and logic circuitry can be used to sense the inspiration portion of the person's 26 breathing cycle. If breathing ceases, the breathing stopped indicator 56 would signify the presence of apnea. Continuous oxygen switch 72 can be used to supply oxygen continuously to the person 26 by directly controlling solenoid valve 14.

We claim:

1. In an in vivo respiratory system, a method of supplying a mass of breathing gas, such as oxygen, to a person during each of the very initial stages of such person's inspiration cycles to maintain the proper arterial oxygen tension in such person's bloodstream and to significantly reduce the consumption of oxygen by such person without reducing thereby such arterial oxygen tension required to be maintained in such person's bloodstream to support life, comprising the steps of:
   supplying such person the mass of oxygen by connecting such person to said source of breathing gas;
   using valve means to control the mass of oxygen being supplied to such person;
   flowing such gas through mass flow sensing means to derive an electrical output voltage proportional to the magnitude and direction of such mass flow of gas through said mass flow sensing means;
   operatively associating circuitry means with said valve means to control said valve means;
   inputting such electrical output voltage derived from said mass flow sensing means to said circuitry means to thereby control said valve means;
   operatively associating heater means with said mass flow sensing means;
   thermally connecting upstream and downstream active resistor arms of a Wheatstone bridge with said Wheatstone bridge determining mass flow;
   operatively associating heater control circuit means with said upstream and downstream active resistor arms of said Wheatstone bridge to lower the resistance of said upstream active resistor arm more than the resistance of said downstream active resistor arm when gas flows through said mass flow sensing means to thereby unbalance said Wheatstone bridge by an amount proportional to the mass of gas flowing through said mass flow sensing means thereby causing said heater means to heat such flowing mass of gas; and
   operatively associating two resistor arms of said Wheatstone bridge with sensing bridge supply circuit means.

2. The method of claim 1 wherein in said step of operatively associating circuitry means with said valve means to control said valve means, said circuitry means opens said valve means during such person's inspiration cycle to connect such person to said source of breathing gas to supply said mass of breathing gas to such person.

3. The method of claim 1 wherein in said step of using valve means to control the mass of oxygen being supplied to such person, said valve means selectively supplies oxygen to said respiratory system during each of said very initial stages of such person's inspiration cycles.

4. The method of claim 1 wherein in said step of operatively associating heater control circuit means, said heater means keeps the temperature of said mass flow sensing means at a constant differential above the ambient air temperature under varying temperature and air flow.

5. The method of claim 1 wherein in said step of operatively associating circuitry means with said valve means to control said valve means, said circuitry means senses apnea by detecting such person;s missing inspiration cycle.

6. The method of claim 5, wherein said circuitry means provides an alarm upon sensing apnea.

7. The method of claim 5, wherein said circuitry means provides visual indication of apnea upon sensing apnea.

8. The method of claim 1 wherein said in said step of operatively associating circuitry means with said valve means to control said valve means, said circuitry means actuates and opens said valve means to supply oxygen to such person corresponding to the breathing rate and intensity of such person's inspired breath.

9. In an in vivo respiratory system, an apparatus for supplying a mass of breathing gas, such as oxygen, to a person during each of the very initial stages of such person's inspiration cycles to maintain the proper arterial oxygen tension in such person's bloodstream and to significantly reduce the consumption of oxygen by such person without reducing such arterial oxygen tension required to be maintained in such person's bloodstream to support life; said apparatus comprising a source of breathing gas, valve means, mass flow sensing means, circuitry means, heater means, a Wheatstone bridge, heater control circuitry means and sensing bridge supply circuit means; said source of breathing gas being in communicative relationship with such person to supply such person the mass of oxygen, said valve means controlling the mass of oxygen supplied to such person, said mass flow sensing means receiving such gas in flowing relationship therethrough to derive an electrical output voltage proportional to the magnitude and direction of such mass of gas flowing through said mass flow sensing means, said circuitry means operatively controlling said valve means by said electrical output voltage derived from said mass flow sensing means being inputted to said circuitry means, said heater means being operatively associated with said mass flow sensing means, said Wheatstone bridge having thermally connected upstream and downstream active resistor arms and said Wheatstone bridge determining mass flow, said heater control circuit means having operatively associated therewith said upstream and downstream active resistor arms of said Wheatstone bridge to lower the resistance of said upstream active resistor arm more than the resistance of said downstream active resistor arm when gas flows through said mass flow sensing means to thereby unbalance said Wheatstone bridge by an amount proportional to the mass of gas flowing through said mass flow sensing means thereby causing said heater means to heat such flowing mass of gas, and said sensing bridge supply circuit means having operatively associated therewith two resistor arms of said Wheatstone bridge.

10. An apparatus in accordance with claim 9, wherein sid circuitry means in controlling said valve means opens said valve means during such person's inspiration cycles to connect such person to said source of breathing gas to supply said mass of breathing gas to such person.

11. An apparatus in accordance with claim 9, wherein said valve means selectively supplies oxygen to said respiratory system during each of the very initial stages of such person's inspiration cycles.

12. An apparatus in accordance with claim 9, wherein said heater means maintains the temperature of said mass flow sensing means
   at a constant differential above the ambient air temperature under varying temperature and air flow.

13. An apparatus in accordance with claim 9, wherein said circuitry means senses apnea by detecting such person's missing inspiration cycle.

14. An apparatus in accordance with claim 13, wherein said circuitry means provides an alarm upon sensing apnea.

15. An apparatus in accordance with claim 13, wherein said circuitry means provides visual indication of apnea upon sensing apnea.

16. An apparatus in accordance with claim 9, wherein said circuitry means actuates and opens said valve means to supply oxygen to such person corresponding to the breathing rate and intensity of such person's inspired breath.

* * * * *